United States Patent
Ehbets et al.

(10) Patent No.: US 7,466,417 B2
(45) Date of Patent: Dec. 16, 2008

(54) PROCESS FOR THE COLOUR MEASUREMENT OF PRINTED SAMPLES INCLUDING BRIGHTENERS

(75) Inventors: Peter Ehbets, Zurich (CH); Beat Frick, Buchs (CH); Mark Wegmüller, Zurich (CH); Adrian von Orelli, Zurich (CH)

(73) Assignee: X-Rite Europe GmbH, Regensdorf (CH)

( * ) Notice: Subject to any disclaimer, the term of this patent is extended or adjusted under 35 U.S.C. 154(b) by 241 days.

(21) Appl. No.: 11/581,027

(22) Filed: Oct. 13, 2006

(65) Prior Publication Data

US 2007/0086009 A1    Apr. 19, 2007

(30) Foreign Application Priority Data

Oct. 17, 2005   (EP)   ................... 05022584

(51) Int. Cl.
*G01J 3/50* (2006.01)
(52) U.S. Cl. ......................... 356/402; 356/73
(58) Field of Classification Search ................. 356/402, 356/73
See application file for complete search history.

(56) References Cited

U.S. PATENT DOCUMENTS

| | | | |
|---|---|---|---|
| 4,699,510 A | 10/1987 | Alguard | |
| 5,636,015 A * | 6/1997 | Imura et al. | ................... 356/72 |
| 6,020,959 A | 2/2000 | Imura | |
| 2002/0135768 A1 | 9/2002 | Sugiyama et al. | |
| 2003/0169421 A1 | 9/2003 | Ehbets | |

OTHER PUBLICATIONS

European Search Report dated Feb. 27, 2006.

* cited by examiner

*Primary Examiner*—F. L Evans
(74) *Attorney, Agent, or Firm*—McCarter & English, LLP

(57) ABSTRACT

For the color measurement of samples printed on a substrate including a brightener, a raw spectral reflection factor of the sample is measured in a first measurement by illumination of the sample with light without UV portion. In a second measurement, a fluorescence spectrum of the sample is measured by illumination of the sample with only UV light. The measured fluorescence spectrum is recalculated as a corrected fluorescence spectrum by weighting with spectrally dependent correction factors and, finally, the measured raw spectral reflection factor and the corrected fluorescence spectrum are added to form a corrected spectral reflection factor from which the values characterizing the color of the sample are then calculated. The spectral correction factors are determined during the device manufacture for a certain set of light types and stored in the device.

22 Claims, 3 Drawing Sheets

PROCESS FOR THE COLOUR MEASUREMENT OF PRINTED SAMPLES INCLUDING BRIGHTENERS

Figure 1:
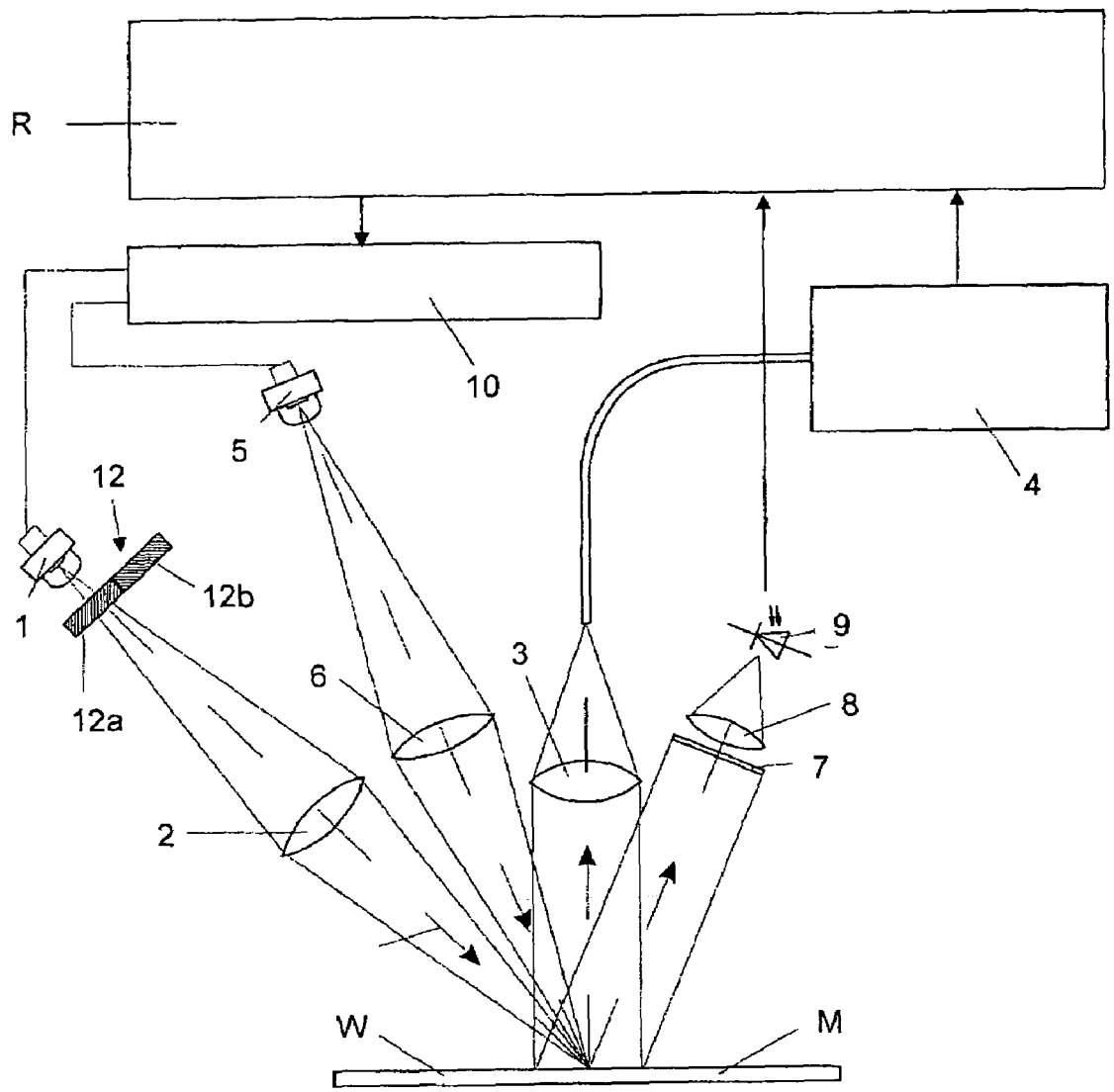

The invention relates to a process for the colour measurement of samples printed onto substrates with brighteners.

Optical brighteners are used more and more often during the manufacture of paper. Optical brighteners can improve the degree of brightness of the paper (generally the substrate) and lower the manufacturing cost.

Optical brighteners absorb light in the ultraviolet (UV-) wavelength range of 320 to 410 nm and re-emit fluorescence light in the visual blue spectral range between 420 to 550 nm. The maximum of the fluorescence spectrum lies between 430 and 440 nm.

The effect of optical brighteners and the generated paper colour are strongly influenced by the spectral distribution of the illumination light, in particular by the ratio of the light levels in the UV and blue spectral ranges. The colour reproduction on printed samples is additionally influenced by the absorption behavior of the colour layer on the paper substrate.

The non-linear behavior of the optical brighteners places high demands on the colour measurement technology. The goals of colour measurement technology are on the one hand to obtain data which correlate well with a certain visual observation with defined illumination spectrum. On the other hand, it is important for process control and measurement data exchange that different measurement apparatus and further same sample output data which are as identical as possible.

The current situation of the colour measurement technology is satisfactory for printed samples on substrates without optical brighteners. When optical brighteners are used, larger, non-satisfactory deviations of the data occur.

It is important for good device conformity that the illumination spectra in the devices have identical relative distribution in the UV and blue spectral ranges. Larger differences between the different measurement devices occur especially in the UV range.

It is further demanded for compatibility of the visual observation that the illuminations in the device and for the observation are identical. The realization of this situation is technically very demanding, since the external illumination conditions are variable.

Actual hand held colour measurement devices such as the SpectroEye of the company Gretag-Macbeth AG use an incandescent bulb as light source. This device includes a filter wheel in the measurement optics. The illumination spectrum and the receiver characteristic can be modified with different measurement filters. It is recommended for a good device conformity to measure brightened samples with the built in UV blocking filter. This filter eliminates the UV portion of the illumination light so that the optical brightener cannot produce any fluorescence. The requirements for an exact control of the illumination spectrum are obviated. It is however problematic with the UV blocking filter method that the data do not correspond with real observation conditions, since typical light sources include at least a UV portion and therefore excite the brighteners.

Exact measurement results are made possible with the so called bi-spectral measurement method. A bi-spectral measurement device has a monochromator in the illumination optics and a spectral analyzer in the receiver channel. The measurement is carried out sequentially. A complete reflection spectrum is measured for each illumination wavelength and stored in the form of a matrix. The resulting reflection spectrum of the sample is determined by multiplication of the matrix with a vector which represents the spectral optical energy distribution of the demanded light type. This measurement technology includes no limitation; the sequential measurement course is however time consuming. Realization of this measurement technology is expensive, so that it is out of the question for industrial use. Examples for a bi-spectral measurement system are the devices BFC-450 of the company Labsphere and CM-3800 of the company Minolta.

U.S. Pat. No. 6,844,931 describes a colour measurement system with variable light emitting diode (LED) illumination and a spectral analyzer in the receiver. The LED light source consists of a multiplicity of differently coloured, white and UV-LEDs. The individual LEDs can be individually controlled so that the spectral illumination distribution can be electronically adapted to the desired spectrum. The determination of the spectral reflection factor of the sample is then carried out with a single measurement with the desired illumination spectrum.

It is an object of the present invention to provide a process for the colour measurement of brightened samples, which improves the precision of the data and at the same time can be simply and cost efficiently implemented relative to known measurement processes.

In general, the process in accordance with the invention determines the spectral reflection factor of the sample with a double measurement and combination of the data obtained thereby. In the first measurement, the spectral reflection factor is determined with the generally known UV-blocking filter technology. In the second measurement, one illuminates only with UV light and the fluorescence spectrum is separately measured. The fluorescence spectrum is then weighted with spectrally dependent correction factors and added to the spectral reflection factor of the UV-blocking filter measurement. The spectral correction factors are determined during manufacture of the device for a certain set of light types and stored in the device.

The measurement process in accordance with the invention provides several advantages:

It can be implemented relatively simply in existing devices with exchangeable measurement filters, for example the already mentioned SpectroEye.

The measurement process can also be realized with two different light sources with different emission spectrum, for example by the combination of UV-LED with white LED.

The requirement for a good spectral conformity of the illumination spectrum in the device is obviated by the separate evaluation of the fluorescence spectrum and the UV-blocking filter measurement. Deviations between different devices can be compensated by the correction factors so that a very high device conformity is achieved.

The storage of one set of correction factors for different light types enables by way of a single double measurement the output of equivalent spectra and colour values for all light types. This function enables an evaluation of the colour reproduction properties of the sample under different observation conditions and is very useful for the selection of the colours and the printing process for the reproduction of the original.

The measurement process is also sensible for the use in an automated colour measurement system for the scanning of printed colour charts for the calibration of printers. Colour profiles for different light types can be produced by way of the double measurement data and a colour management software.

The presence of an illumination only in the UV range enables furthermore the measurement of printed security features which are produced by excitation in the UV range.

Figure 2:
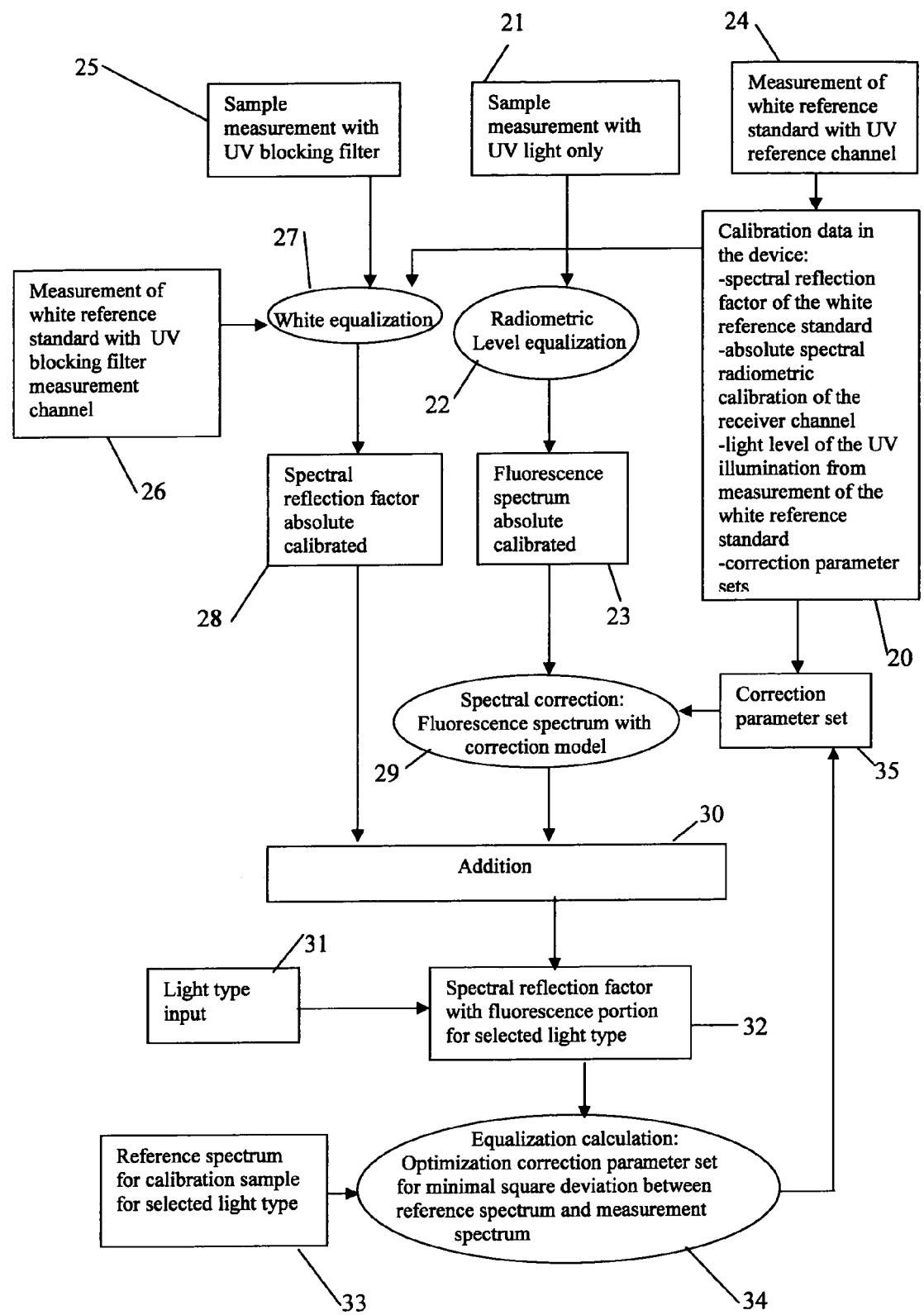
Figure 3:
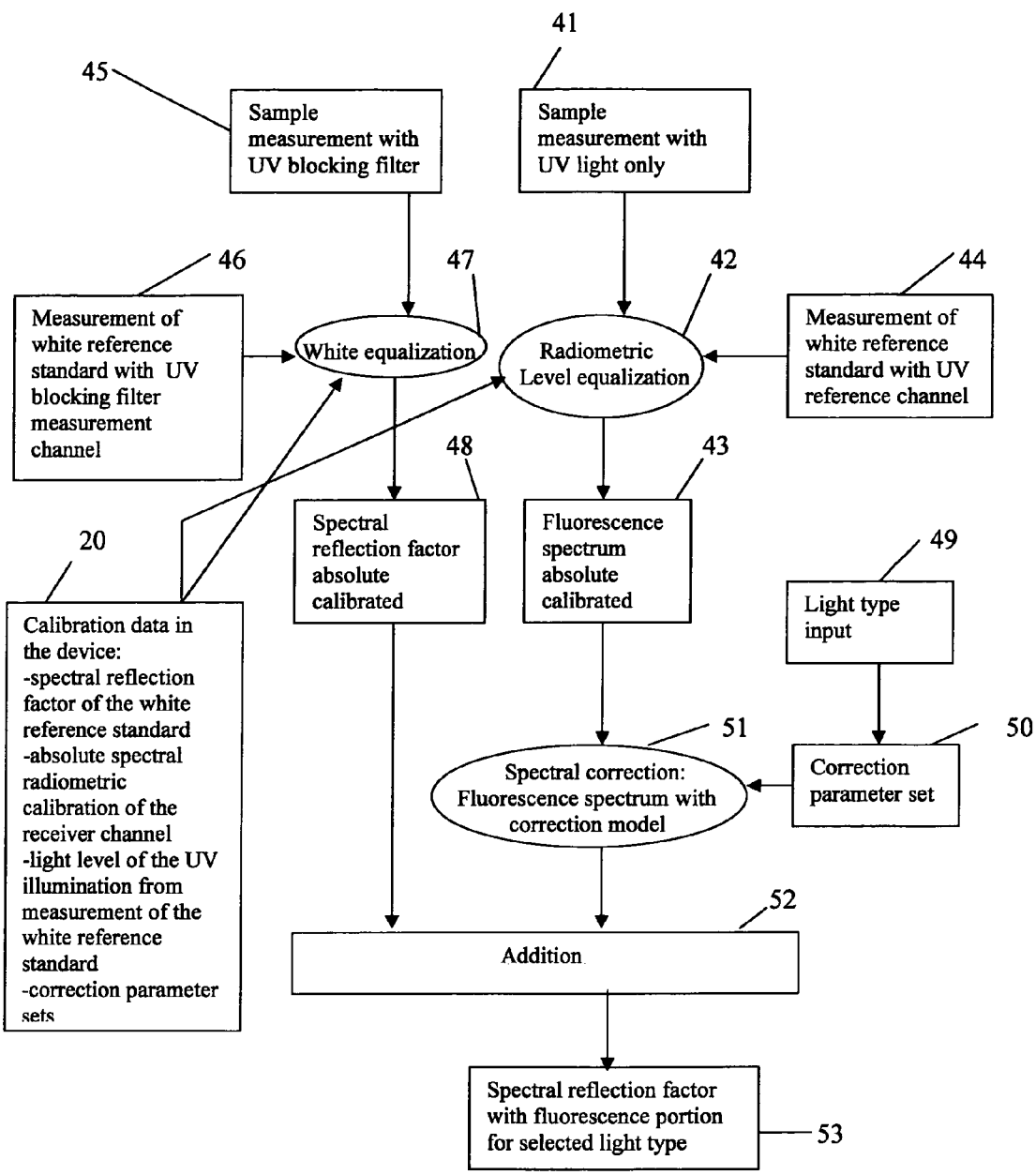

The invention is in the following further described by way of the drawings. It shows:

FIG. 1 a schematical illustration of the most important components of a measurement arrangement suitable for the measurement process in accordance with the invention;

FIG. 2 a block diagram of the determination of the correction parameters used in the correction process in accordance with the invention; and FIG. 3 a block diagram of an exemplary embodiment of the measurement process in accordance with the invention.

As is known, different measurement arrangements (measurement geometries) are used in the colour measurement technology: diffuse measurement geometries with Ulbricht sphere, 45°/0°-measurement geometry and goniometrical measurement processes with more than one measurement angle. The measurement arrangements are defined in different standards or recommendations, for example in the publication CIE 15 of the Commission International d'"Eclairage and in the standard DIN 5033, part 7. The measurement device illustrated in FIG. 1 and suitable for the measurement process in accordance with the invention principally follows the known measurement geometries.

Concretely, the measurement device includes a first light source 1, a first illumination optics 2, a first pickup optics 3, a first photoelectric converter 4, a second light source 5, a second illumination optics 6, a UV filter 7, a second pickup optics 8, a second photoelectric converter 9, a lamp controller 10 and a computer for the control of the photoelectric converter and for the digitalization and further processing or storage of the measurement signals produced by the photoelectric converters. The first light source 1, first illumination optics 2, first pickup optics 3 and the first converter 4, together form a first generally known measurement arrangement, which illuminates a measurement object M or sample under an angle of incidence of 45° and captures the measurement light remitted from the measurement object under a remittance angle of 0°. Analagously, the second light source 5, the second illumination optics 6, the UV filter 7, the second pickup optics 8 and the second converter form a second, also generally known measurement arrangement with symmetrical measurement geometry, whereby the angle of incidence of the illumination and the remittance angle of the remitted measurement light are each 30°.

The measurement process in accordance with the invention is described in the following by way of example only and with reference to the measurement configuration of FIG. 1. It is however adaptable to all conventional measurement arrangements.

A light source is typically used for the first light source 1 which has a continuous emission spectrum over the UV and visual spectral range. For example, Xenon-arc lamps or incandescent lamps can be used. The first photoelectric converter 4 is preferably a spectral analyzer which as a minimum is sensitive in the visual spectral range of 400 to 700 nm. The spectral analyzer can be constructed in a generally known manner as spectrometer or calorimeter. The first measurement arrangement fulfills, as already mentioned, the geometric measurement conditions of the standardized 45°/0-geometry.

As will be mentioned further below, two measurements are carried out in the measurement process in accordance with the invention and, in particular one by illumination of the measurement object M with light without UV-portion and one by illumination with only UV light, whereby the sequence of the two measurements is not of importance.

For this purpose, an adjustable filter arrangement 12 is provided in a first variant in the illumination beam path of the first measurement arrangement, which depending on the adjustment is transparent only for visible light or UV light.

The filter arrangement can be implemented, for example, by a filter wheel with two suitable filters, as already used in the above mentioned device "SpectroEye". One of the two filters 12a of the filter arrangement 12 is a UV blocking filter which is constructed as an edge filter, which suppresses illumination light below 400 nm and has a good transmission throughout the visible range. The other filter 12b of the filter arrangement 12 is an edge filter complimentary thereto which suppresses the light with a wavelength above 400 nm and is as transparent as possible for UV light. This filter (UV transmission filter) can also be constructed in such a way that it enables a better adaptation of the illumination spectrum in the UV range to a desired reference light type. As already mentioned, a UV-blocking filter is first used for the double measurement and then a UV-transmission filter is used, or vice-a-versa.

A suitable switchable UV/non-UV double illumination can be carried out according to a second variant by way of two or more different light sources, which can be individually switched on and off. A part of the light sources can thereby be emitting light only in the UV range and the other part of the light sources only in the visible range. This can be realized in that continuous light sources with permanently installed filters are used. Alternatively, light sources can be used which have a spectrally limited emission spectrum without additional filtering. Light sources of this type are light emitting diodes (LEDs). The UV-LEDs NCCU033(T) and NCCU001E of the manufacturer Nichia with peak wavelengths of 365 nm or 380 nm can be used, for example, individually or in combination. The UV blocking filter characteristic can be realized, for example, with white LEDs which are sold by the manufacturer Lumileds under the product name Luxeon. These white LEDs have a continuous emission spectrum in the range of 420 mn to 700 nm. A possible implementation for a double illumination with controlled light sources by use of the second measurement arrangement 5-9 is symbolized in FIG. 1. The filter arrangement 12 is thereby of course obviated.

The illumination and measurement with UV light need not conform to the 45°/0° standard geometry and the measurement light can be applied to the measurement object at any angle. When separate light sources are used for the UV light and visible light, it is therefore possible to arrange the UV light sources at an angle below 45°, for example 30°, whereby often a more compact construction of the measurement device can be achieved.

It is required for the process in accordance with the invention that the measurement device further include a white reference standard W which is standardized for the absolute reflection factor. The white reference standard can also consist of a white ceramic tile, as known in the art, which was calibrated with a calibrated spectrophotometer. When measurements are carried out on the white reference standard W, it takes the place of the actual measurement object M.

It is further required that the measurement device include a UV reference channel for the UV light source, which serves to monitor the light level of the UV light source over the life of the device and to detect level variations. The level variations are taken into consideration by the measurement system during the measurement data calculation. The UV reference channel can be realized with a spectral photoelectric converter 4, if the latter is only sensitive in the UV range and if the white reference standard W has a sufficient reflection factor in the UV range. Alternatively, the UV reference channel can be realized with a photo diode (converter 9) which is sensitive in the UV range and measures the light reflected by the white reference standard. A third possibility for the realization of the UV reference channel is the installation of a fluorescence sample which is excited in the UV range and generates light in the visible range. The visible fluorescence portion can then be measured by way of the spectral receiver (converter 4). Suitable fluorescence standards are offered for sale, for example, by the company Labsphere under the product name Spectralon.

To carry out the double measurement, the receiver channel (formed by the pickup optics and the spectralconverter) must be radiometrically calibrated. The radiometric calibration is carried out in that a continuous light source with known spectral signal distribution (reference spectrum) is measured with the receiver channel. The radiometric calibration is carried out in a generally known manner by the quotient of the reference spectrum and the corresponding digitalized (spectral) data of the receiver.

At the end of the production course of the measurement device, the correction factors required for the measurement process in accordance with the invention for the linking of the fluorescence spectrum with the UV locking filter reflection spectrum are determined during the device calibration. A set of brightened colour samples (colour samples printed onto a substrate including brighteners) is measured for the calibration with a reference device with known illumination or by a bi-spectral process. The set of probes includes at least one substrate or paper type with optical brighteners typical for the application. The measured reference reflection spectra are determined for the desired light types over the visible range and stored.

The calibration sample set is then measured with a measurement device according to the following sequence which is schematically summarized in FIG. 2:

A measurement of the white reference standard W is first carried out with the UV illumination. This step corresponds to Block 24. The light level is measured with the UV reference panel and the corresponding measured value is then stored in the calibration data (Block 20). A measurement of the white reference standard W is then carried out with the UV blocking filter measurement channel. The corresponding spectral measurement values are stored (Block 26).

The fluorescence spectrum of each (calibration) sample is measured in a next step with the UV-illumination (Block 21) and converted into energetic units (Block 22) by way of the radiometric standardization of the spectral receiver and stored (Block 23). The radiometric standardization is stored in the calibration data of the device (Block 20). The UV illumination is carried out at the same light level as for the white reference measurement (Block 24). The light level is controlled by the control electronics 10.

The spectral reflection factor of the sample is then measured in a generally known manner in the UV-blocking filter mode (illumination only with visible light). The measured values (Block 25) are transformed into absolute units of the spectral reflection factor (Block 27) by comparison with the reference white measurement (Block 26) and the calibration data of the white reference standard. The resulting spectral reflection factors are stored (Block 28).

The fluorescence spectrum (Block 23) is then corrected by way of a correction model (Block 29) and the measurement spectra formed from the sum of the spectral reflection factors in the UV-blocking filter mode and the corrected fluorescence spectra (Block 30).

The correction mode for the fluorescence spectrum includes spectrally dependent scaling factors which adapt the relative distribution of the fluorescence spectrum. The spectral scaling factors include a variable for each spectral measurement value in the range of 420 nm to 550 nm. The absolute level is additionally adapted with a global scaling factor.

The scaling factors are in the following also referred to as correction parameters (for the correction model).

The following steps are carried out for different light types (Block 31), whereby a corresponding set of correction factors (scaling factors) is calculated and stored for each light type.

The calculation of the scaling factors is carried out by way of a generally known equalization calculation (Block 34) by way of the previously determined corrected spectral reflection factor with fluorescence portion for the selected light type (Block 32) and the mentioned reference spectrum for the same light type (Block 33), whereby the scaling factors are the variables of the equalization calculation which are to be determined. The equalization calculation is thereby carried out in a generally known manner in such a way that the differences between the measurement spectra (Block 32) and the reference spectra (Block 33) are minimized (for example minimal square deviation). The result of the equalization calculation then delivers the variables or scaling factors as correction parameter set for the respective light type (Block 35). The correction parameter sets for the individual light types are then stored in the calibration data of the device (Block 20) for use in the measurement process in accordance with the invention.

When the conformity achieved in the equalization calculation is not satisfactory, additional correction parameters and dependencies can be introduced into the correction model. For example, an additional dependency of the correction factors as a function of the spectral reflection factor of the sample can be introduced.

After these preparatory steps, an actual sample measurement can be carried out according to the measurement process in accordance with the invention. The individual steps of the process are schematically summarized in FIG. 3.

A measurement on the calibrated right reference standard W is first carried out for the double measurement during use.

The reflected light level of the UV light source is first determined with this measurement (Block 44). The spectral measurement values for the white reference standard are then measured with the UV blocking filter measurement channel (Block 46).

After the white measurement, sample measurements can be carried out. These measurements are carried out as double measurements with UV blocking filter (Block 45) and only with UV light (Block 41). Both measurements are carried out with the same light level as for the white measurement. The light levels are maintained constant by the control electronics 10.

The sample measurement with UV blocking filter is transformed by a white equalization (Block 47) into absolute reflection spectra (Block 48). This white equalization is carried out by the multiplication of the sample measurement values in the UV blocking filter mode with the quotient of the spectral reflection factor in the calibration data of the device (Block 20) and the white measurement (Block 46).

The sample measurement without UV light is converted by way of a radiometric level equalization (Block 42) into a radiometric fluorescence spectrum (Block 43). The radiometric level equalization includes the multiplication of the sample measurement without UV light (Block 41) with the radiometric standardization in the calibration data in the device (Block 20). Additionally, the light level is corrected in that the fluorescence spectrum is multiplied with the quotient of the light level of the white measurement (Block 44) and the light level in the calibration data (Block 20).

A desired light time can be selected (Block 49) by way of the device input or a software interface.

The corresponding set of correction parameters is loaded (Block 50) from the calibration data in the device (Block 20).

The correction parameter set is used in the correction model for the absolute fluorescence spectra (Block 51).

The spectral reflection factor in the UV-blocking filter mode (Block 48) and the corrected fluorescence spectrum (Block 51) are added (Block 52) and transformed into the reflection spectrum with the defined fluorescence portion for the desired light type (Block 53).

With the help of the correction factors in the calibration data, the equivalent spectral reflection factors for the desired light types can now be determined and displayed for each sample measurement.

The reflection spectra so determined can be calorimetrically evaluated in a generally known manner, for example for the calculation of colour values. Furthermore, quality parameters for the colour reproduction of the sample, for example a Metameric-Index or Colour Inconstancy Index can be determined in a generally known manner for different light types by way of only a single double measurement.

The invention claimed is:

1. Process for the colour measurement of samples printed on substrates with brighteners, whereby a spectral reflection factor of a sample is determined and made available for the calculation of values characterizing the colour, characterized in that the spectral reflection factor of the sample is determined by way of a double measurement, whereby in a first measurement a raw spectral reflection factor of the sample is measured by illumination of the sample with light without UV portion, a fluorescence spectrum of the sample is measured in a second measurement by illumination of the sample with only UV light, the measured fluorescence spectrum is recalculated as a corrected fluorescence spectrum by way of a correction model in which the fluorescence spectrum is spectrally weighted with a set of spectrally dependent correction factors, and whereby the measured raw spectral reflection factor and the corrected fluorescence spectrum are added to form a corrected spectral reflection factor which corrected spectral reflection factor is used for the calculation of the values characterizing the colour of the sample.

2. Process according to claim 1, characterized in that individual sets of correction factors are used for the correction model for different light types and that respectively one corrected spectral correction factor is calculated for one or more select light types by using the individual set of correct parameters associated with the respective light type.

3. Process according to claim 1, characterized in that the correction factors are determined from the corrected spectral reflection factor and a reference spectrum of a calibration sample as the result of an equalization calculation in which the deviations between the corrected spectral reflection factor and the reference spectrum are minimized.

4. Process according to claim 1, characterized in that a continuous light source emitting also in the UV range and with exchangeable filters is used for the measurement of the raw spectral reflection factor and the fluorescence spectrum, whereby one of the filters blocks UV light and another filter blocks non-UV light.

5. Process according to claim 1, characterized in that several selectively activatable light sources with spectrally different emission spectra are used for the measurement of the raw spectral reflection factor and the fluorescence spectrum, whereby at least one light source emits in the UV range.

6. Process according to claim 5, characterized in that UV light emitting diodes and white light emitting diodes are used as light sources.

7. Process according to claim 5, characterized in that the light source emitting in the UV range impinges the sample at an especially small angle of incidence deviating from the standard geometry.

8. Process according to claim 6, characterized in that the light source emitting in the UV range impinges the sample at an especially smaller angle of incidence deviating from the standard geometry.

9. Process according to claim 1, characterized in that the signal level of the UV illumination light is monitored by way of a UV reference measurement channel and taken into consideration in the measurement.

10. Process according to claim 1, characterized in that the signal level of the UV illumination light is monitored by way of a fluorescence standard and taken into consideration in the measurement.

11. Process according to claim 1, characterized in that one or more quality parameters are calculated for the colour reproduction of the sample from the corrected spectral reflection factor for one or more light types.

12. Process for the colour measurement of samples (M) printed on substrates with brighteners, whereby a spectral reflection factor of a sample (M) is determined and made available for the calculation of values characterizing the colour, characterized in that the spectral reflection factor (53) of the sample (M) is determined by way of a double measurement, whereby in a first measurement (45) a raw spectral reflection factor (48) of the sample (M) is measured by illumination of the sample (M) with light without UV portion, a fluorescence spectrum (43) of the sample (M) is measured in a second measurement (41) by illumination of the sample (M) with only UV light, the measured fluorescence spectrum (43) is recalculated as a corrected fluorescence spectrum by way of a correction model (51) in which the fluorescence spectrum (43) is spectrally weighted with a set of spectrally dependent correction factors (50), and whereby the measured raw spectral reflection factor (48) and the corrected fluorescence spectra are added to form a corrected spectral reflection factor (53), whereby the corrected spectral reflection factor (53) is used for the calculation of the values characterizing the colour of the sample (M), whereby individual sets of correction factors (50) for the correction model (51) are used for different light types (49) and that respectively one corrected spectral reflection factor (53) is calculated for one more selected light types using the individual sets of correction parameters (50) associated with the respective light type, and whereby the correction factors (50) are determined from the correct spectral reflection factor (53) and a reference spectrum (33) of a calibration sample as a result of an equalization calculation (34) wherein the deviations between the corrected spectral reflection factor (53) and the reference spectrum (33) are minimized.

13. Process according to claim 12, characterized in that a continuous light source (1) with exchangeable filters (12) which also emits in the UV range is used for the measurement of the raw spectral reflection factor (48) and the fluorescence spectrum, whereby one of the filters (12a) blocks UV light and another filter (12b) blocks non-UV light.

14. Process according to claim 12, characterized in that several selectively activatable light sources (1,5) with spectrally different emission spectra are used for the measurement of the raw respective reflection factor (48) and the fluorescence spectrum, whereby at least one light source (5) emits in the UV range.

15. Process according to claim 14, characterized in that UV light emitting diodes and white light emitting diodes are used as light sources (1,5).

16. Process according to claim 14, characterized in that the light source (5) emitting in the UV range impinges the sample (M) under an especially smaller angle of incidence deviating from the 45°/0° standard geometry.

17. Process according to claim 15, characterized in that the light source (5) emitting in the UV range impinges the sample (M) under an especially smaller angle of incidence deviating from the 45°/0° standard geometry.

18. Process according to claim 12, characterized in that the signal level of the UV illumination light is monitored by way of a UV reference channel (4,9) and taken into consideration for the measurement.

19. Process according to claim 12, characterized in that the signal level of the UV illumination light is monitored by way of a fluorescence standard and taken into consideration for the measurement.

20. Process according to claim 12, characterized in that one or more quality parameters for the colour reproduction of the sample (M) are calculated from the corrected spectral reflection factor (54) for one or more light types.

21. Process according to claim 12, characterized in that the reflection of a white reference standard (W) is measured with a spectrophotometer of a receiver channel.

22. Process according to claim 21, characterized in that the white reference standard (W) is a white ceramic tile or a white pill.

* * * * *